(12) United States Patent
Faig et al.

(10) Patent No.: US 10,813,875 B2
(45) Date of Patent: Oct. 27, 2020

(54) MEMORY SHAPE SUNSCREEN COMPOSITION

(71) Applicant: L'OREAL, Paris (FR)

(72) Inventors: Jonathan James Faig, Sayreville, NJ (US); David Chan, Edison, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/959,938

(22) Filed: Apr. 23, 2018

(65) Prior Publication Data

US 2019/0321280 A1   Oct. 24, 2019

(51) Int. Cl.
| | | |
|---|---|---|
| A61K 8/87 | (2006.01) | |
| A61K 8/35 | (2006.01) | |
| A61Q 17/04 | (2006.01) | |
| A61K 8/37 | (2006.01) | |
| A61K 8/40 | (2006.01) | |
| A61K 8/81 | (2006.01) | |

(52) U.S. Cl.
CPC .......... *A61K 8/87* (2013.01); *A61K 8/35* (2013.01); *A61K 8/37* (2013.01); *A61K 8/375* (2013.01); *A61K 8/40* (2013.01); *A61K 8/8182* (2013.01); *A61Q 17/04* (2013.01)

(58) Field of Classification Search
CPC ........ A61K 8/35; A61K 8/375; A61K 8/8182; A61K 8/87; A61K 8/40; A61K 8/60; A61K 8/37
See application file for complete search history.

(56) References Cited

U.S. PATENT DOCUMENTS

| | | |
|---|---|---|
| 4,195,999 A | 4/1980 | Adachi et al. |
| 4,427,836 A | 1/1984 | Kowalski et al. |
| 4,469,825 A | 9/1984 | Kowalski et al. |
| 4,594,363 A | 6/1986 | Blankenship et al. |
| 4,677,003 A | 6/1987 | Redlich et al. |
| 4,920,160 A | 4/1990 | Chip et al. |
| 4,970,220 A | 11/1990 | Chaussee |
| 4,970,241 A | 11/1990 | Kowalski et al. |
| 5,157,084 A | 10/1992 | Lee et al. |
| 5,624,663 A | 4/1997 | Deflandre et al. |
| 5,663,213 A | 9/1997 | Jones et al. |
| 6,165,450 A | 12/2000 | Chaudhuri et al. |
| 2004/0228811 A1 | 11/2004 | Krzysik |
| 2010/0189661 A1 | 7/2010 | Musa et al. |
| 2011/0064681 A1 | 3/2011 | Wendel et al. |
| 2016/0002384 A1* | 1/2016 | Nacharaju ............ A61K 9/0014 525/150 |
| 2016/0362630 A1 | 12/2016 | Holland et al. |
| 2017/0100315 A1* | 4/2017 | Dickhof ................. A61K 8/062 |
| 2017/0281488 A1 | 10/2017 | Halpern Chirch et al. |
| 2017/0327623 A1* | 11/2017 | Paczkowski ............ A61K 8/87 |

FOREIGN PATENT DOCUMENTS

| | | |
|---|---|---|
| DE | 19746654 A1 | 2/1999 |
| DE | 19755649 A1 | 6/1999 |
| DE | 19855649 A1 | 6/2000 |
| DE | 10162844 A1 | 7/2003 |
| EP | 0267726 A2 | 5/1988 |
| EP | 0331421 A2 | 9/1989 |
| EP | 0832642 A2 | 4/1998 |
| EP | 0967200 A1 | 12/1999 |
| EP | 1008586 A1 | 6/2000 |
| EP | 1027883 A2 | 8/2000 |
| EP | 1092421 A2 | 4/2001 |
| EP | 1133980 A2 | 9/2001 |
| EP | 1133981 A2 | 9/2001 |
| EP | 1300137 A2 | 4/2003 |
| GB | 2338650 | 12/1999 |
| JP | 2016084330 A | 5/2016 |
| WO | 9304665 A1 | 3/1993 |
| WO | 2004006878 A1 | 1/2004 |
| WO | 2008090066 A2 | 7/2008 |
| WO | 2009027258 A2 | 3/2009 |
| WO | 2011113718 A1 | 9/2011 |
| WO | 2019014568 A1 | 1/2019 |

OTHER PUBLICATIONS

Arlacel C, U.S. National Library of Medicine, https://pubchem.ncbi.nlm.nih.gov/compound/6433515#section=Top, accessed Feb. 1, 2018, 16 pgs.
Arlacel LC by Croda Inc.—Personal Care & Cosmetics, https://www.ulprospector.com/en/na/PersonalCare/Detail/134, accessed Feb. 1, 2018, 3 pgs.
Arlacel 165 by Croda-Household, Industrial & Institutional Cleaners, https://www.ulprospector.com/en/na/Cleaners/Detail/976/75456/Arlacel-165, accessed Feb. 1, 2018, 2 pgs.
Arlacel 170, Croda Personal Care::Product Finder, https://www.crodapersonalcare.com/home.aspx?view=dtl&D-contents, accessed Feb. 1, 2018, 2 pgs.
Aristoflex AVC, AAko, https://www.aako.nl/product=groups/personal-hair-care/products, accessed Feb. 1, 2018, 3 pgs.
Emulium Mellifera product information sheets, obtained Feb. 1, 2018, 6 pgs.
ADEKA, Who We Are information sheet, obtained Feb. 1, 2018, 2 pgs.
ADEKA NOL GT-730, Data information Sheets, Dec. 4, 2014, 3 pgs.

(Continued)

*Primary Examiner* — Mina Haghighatian
(74) *Attorney, Agent, or Firm* — McNees Wallace & Nurick LLC

(57) ABSTRACT

A memory-shape skin-care composition, in the form of an oil-in-water emulsion, including a UV filter system, including avobenzone, octocrylene, and homosalate. The composition additionally includes a thickening emulsifier including a co-polymer including a stearate derivative and a polyethylene glycol derivative, a non-thickening emulsifier including a polyglyceryl stearate co-polymer, and a memory-shape material including a polyethylene glycol/hexamethylene diisocyanate co-polymer.

20 Claims, No Drawings

(56) References Cited

OTHER PUBLICATIONS

ADEKA NOL GT-730, Technical Information, Aug. 26, 2014, 6 pgs.
ADEKA NOL GT-730, Reference Information, Oct. 20, 2016, 6 pgs.
"Hydro gelator ADEKA NOL GT-730", Aug. 26, 2014, pp. 1-6.
Mintel, "Smart Gel", Jan. 23, 2013.
Mintel, "Moist Wrap BB Gel SPF 32 PA+++", Aug. 11, 2017.
International Search Report for PCT/US2019/025794, dated Jun. 28, 2019.

* cited by examiner

MEMORY SHAPE SUNSCREEN COMPOSITION

FIELD OF THE INVENTION

The present invention is directed to skin care compositions.

BACKGROUND OF THE INVENTION

The photoprotection of keratinous substrates, including both skin and hair, is considered by many to be necessary in order to facilitate protection from sun-damage, sunburn, photo-aging, as well as to decrease the chances of skin cancer development caused by exposure to ultraviolet ("UV") radiation. There are typically two types of UV-A/UV-B sunscreen compositions used to accomplish photoprotection, namely, inorganic UV filters and organic UV filters.

Inorganic UV filters such as titanium dioxide and zinc oxide are typically employed in large quantities in order to ensure proper coverage/maximum protection over the surface onto which they are applied. As a result, inorganic UV filters have a tendency to cause skin to which they are applied to feel dry, and further impart an undesirable color onto the treated surface (naturally white, but sometimes colored for aesthetic purposes with varying degrees of aesthetic success).

Further, UV filters may either protect against UV-A radiation (long-wave), UV-B radiation (shortwave), or both. In the past, it was commonly held that protection against UV-B radiation was the primary or even sole consideration in sun-protection. However, more recent research has revealed that exposure to UV-A radiation may also be dangerous and lead to undesirable effects. As such, the current trend in sun-protection endeavors is typically to protect against both UV-A and UV-B in a single composition, and to increase both the SPF and the UV-A ratings of the composition.

Sunscreens are treated as over-the-counter ("OTC") products in many jurisdictions, including in the United States of America ("U. S."). As a result of the classification of sunscreens as OTC products, in the U.S., sunscreen is regulated by the U.S. Food and Drug Administration ("FDA"), which, due to regulatory issues and safety concerns, has limited the active ingredients of sunscreen compositions, such as UV filters, substantially. Thus, there are limited UV filters available to achieve high efficacy with respect to both SPF and UV-A protection. Most commonly, these UV filters are regarded to include avobenzone, oxybenzone, octisalate, octocrylene, and homosalate.

BRIEF DESCRIPTION OF THE INVENTION

In an exemplary embodiment, a memory-shape skin-care composition, in the form of an oil-in-water emulsion, including from 1 to 30 weight percent of a UV filter system, including a UV-A active material and a UV-B active material. The composition additionally includes from 0.2 to 3 weight percent of a thickening emulsifier, from 0.5 to 7 weight percent of a non-thickening emulsifier, and from 0.5 to 7 weight percent of a memory-shape material.

In another exemplary embodiment, a memory-shape skin-care composition, in the form of an oil-in-water emulsion, including from 2 to 25 weight percent of a UV filter system, including avobenzone, octocrylene, and homosalate. The composition additionally includes from 0.2 to 2.5 weight percent of a thickening emulsifier including a co-polymer including a stearate derivative and a polyethylene glycol derivative, from 1 to 5 weight percent of a non-thickening emulsifier including a polyglyceryl stearate co-polymer, and from 3 to 5 weight percent of a memory-shape material including a polyethylene glycol/hexamethylene diisocyanate co-polymer.

Other features and advantages of the present invention will be apparent from the following more detailed description of the preferred embodiment which illustrates, by way of example, the principles of the invention.

DETAILED DESCRIPTION OF THE INVENTION

All numbers expressing quantities of ingredients and/or reaction conditions are understood as being modified in all instances by the term "about", unless otherwise stated.

All SPF and UV-A ratings are provided on the basis of in-vivo value unless otherwise indicated.

In the present application, the term "keratinous substrate," as used herein, includes but is not limited to skin, hair, and nails.

In the present application, the term "ambient temperature" means a temperature of about 25° C.

In the present application, the term "stable" means the emulsion remains intact without phase separation, color and/or odor change over the stability monitoring period and the water-soluble active ingredients remain solubilized in the water phase without crystallization or precipitation out of the emulsion.

In the present application, the term "SPF booster" refers to a material which increases the UV absorption of another material when the two are intermixed in a composition by refracting UV radiation, thereby increasing the effective path length of the UV radiation through the composition.

In the present application, the term "essentially free" indicates that a material is present only in de minimus amounts as an impurity in other ingredients, and the material does not materially affect the properties of the composition.

In the present application, the term "free" indicates that no reliably measurable amount of a material is present in the composition.

The photostable UV-A/UV-B sunscreen composition of the present invention can comprise, consist of, or consist essentially of the essential elements and limitations of the invention described herein, as well as any additional or optional ingredients, components, or limitations described herein or otherwise useful in compositions intended for topical application onto keratinous substrates. In one embodiment, the photostable UV-A/UV-B sunscreen composition includes but is not limited to an oil-in-water or water-in-oil emulsion.

Memory Shape Material (Rheological Modifier)

The composition includes a memory shape material. Memory shape materials exhibit a unique rheology in which the storage modulus and loss modulus are inverted relative to a traditional oil-in-water emulsion, i.e. the loss modulus is greater than the storage modulus. In compositions exhibiting both storage and loss moduli, the storage modulus is associated with solid-like behavior and the loss modulus is associated with fluid-like behavior. Systems in which the loss modulus greater than the storage modulus exhibit fluid-like behavior. In an embodiment, the composition exhibits an inverted storage and loss moduli, which do not cross during storage or use, allowing the composition to exhibit fluid-like behavior at essentially all times.

The memory shape materials are typically in the form of an aqueous gel. The aqueous gel acts as the continuous phase of the oil-in-water emulsion. Although the gel is solid in appearance the higher loss modulus allows the gel to exhibit fluid like behavior and recovery from mechanical stress.

In an embodiment, the memory shape material is formed from a polyether urethane. In some embodiments, the memory shape material includes a polyethylene glycol/hexamethylene diisocyanate co-polymer. In one embodiment, the memory shape material is PEG-240/HDI copolymer bis-decyltetradeceth-20, such as, the product sold under the tradename ADEKA NOL GT-730™. In some embodiments, the memory shape material may be present in an amount by weight of at least 0.5 wt %, at least 1 wt %, at least 2 wt %, at least 3 wt %, less than 15 wt %, less than 12 wt %, less than 10 wt %, less than 7 wt %, less than 6 wt % and/or less than 5 wt %, based on the total weight of the composition.

Emulsifier (Thickening Emulsifier)

In an embodiment, the oil phase includes a thickening emulsifier, such as, non-branched polyol alkyl esters of glycerol and sorbitan esters, including for example glycerol monostearate, such as the product sold under the tradename Arlacel™ 165 by Croda, glyceryl stearate/PEG ester, such as the product sold under the tradename Arlacel™ 170 by Croda, (2R,3R,4R,5S)-hexane-1,2,3,4,5,6-hexol; (Z)-octadec-9-enoic acid, such as the product sold under the tradename Arlacel C by Croda, sorbitan stearate/sorbityl laurate, such as the product sold under the tradename Arlacel LC by Croda, and cetearyl glucoside, such as the product sold under the tradename Tego Care CG90™, glyceryl stearate, steareth-100, glyceryl stearate citrate, and combinations thereof. In some embodiments, the emulsifier may be present in an amount by weight of at least 0.1 wt %, at least 0.3 wt %, at least 0.5 wt %, less than 6 wt %, less than 4 wt %, less than 3 wt %, and/or less than 2.5 wt %, based on the weight of the composition.

Co-Emulsifier (Non-Thickening Emulsifiers)

In an embodiment, the oil phase further includes co-emulsifiers, such as, branched polyol alkyl esters of glycerol and sorbitan esters, including for example polyglyceryl-4 isostearate, such as the product sold under the tradename Isolan® Gl 34 by Evonik, polyglyceryl-3 diisostearate, sold under the tradename Lameform® TGI by BASF, sorbitan isostearate, such as the product sold under the tradename Arlacel™ 987 by Croda, sorbitan glyceryl isostearate, such as the product sold under the tradename Arlacel™ 986 by Croda, and mixtures thereof. Other suitable co-emulsifiers include emulium meliferra, polyglyceryl-4 isostearate, polyglyceryl-4 diisostearate/polyhdroxyl stearate/sebacate, polyglyceryl-10 isostearate, polysorbate-20, polysorbate-40, and/or polysorbate-60. The co-emulsifiers facilitate further stability of the composition. In some embodiments, the co-emulsifiers may be present in an amount of at least 0.1 wt %, at least 0.3 wt %, at least 0.5 wt %, less than 6 wt %, less than 4 wt %, less than 3 wt %, and/or less than 2.5 wt %, based on the weight of the composition.

Thickener (Non-Emulsifying)

The composition may further include additional thickening agents. In some embodiments, the thickening agents may not also act as emulsifiers. In an embodiment, the thickening agent includes a cross-linked vinylpyrrolidone containing polymer. In one embodiment, the thickening agent includes a cross-linked co-polymer of acrylamidomethylpropane sulfonic acid and vinylpyrrolidone reacted in the presence of ammonia, such as, ammonium acryloyldimethyltaurate/vinylpyrrolidone co-polymer sold under the tradename Aristoflex AVC by Aako. In some embodiments, the non-emulsifying thickener may be present in an amount of at least 0.01 wt %, at least 0.03 wt %, at least 0.05 wt %, less than 0.5 wt %, less than 0.3 wt %, less than 0.1 wt %, less than 0.09 wt %, and/or less than 0.08 wt %, based on the weight of the composition.

UV Filter System

UV-Filters, active in UV-A and/or UV-B regions, used for the present invention can be water-soluble, fat-soluble or insoluble in commonly used cosmetic solvents. UV-A filter comprise groups of compounds which absorb light predominantly in the range of wavelengths 400 nm to 320 nm (UV-A) and UV-B filter comprise groups of compounds which absorb light predominantly in the range of wavelengths 400 nm to 320 nm 320 nm to 280 nm (UV-B). According to an embodiment of the invention, UV-A and UV-B can be two separate UV filters or they can be one UV filter with both UV-A and UV-B sun protection factor.

The UV filter may include any suitable UV filter or UV filter system, including, but not limited to, solid organic lipsoluble UV filters, such as, but not limited to, butyl methoxydibenzoylmethane, and ethylhexyl trazone, liposoluble organic UV filters, such as, but not limited to, cinnamate compounds, anthranilates, salicylate compounds, dibenzoylmethane compounds, such as avobenzone, camphor compounds, β,β-diphénylacrylate compounds, triazine compounds, benzotriazole compounds, benzalmalonate compounds (particularly those cited in U.S. Pat. No. 5,624,663), imidazoline compounds, p-aminobenzoate compounds (PABA), benzoxazole compounds (as described in patent applications EP 0832642, EP 1027883, EP 1300137, and DE 10162844), UV-filter polymers and UV-filter silicones (as described in patent application WO-93/04665), α-alkylstyrène dimers (as described in patent application DE 19855649), 4,4-diarylbutadiens (as described in patent applications EP 0967200, DE 19746654, DE 19755649, EP-A-1008586, EP 1133980, and EP 1133981), mérocyanine (as described in U.S. Pat. No. 4,195,999, WO 2004/006878, WO 2008/090066, WO 2011113718, WO 2009027258, and the documents IP COM JOURNAL N° 000179675D published on Feb. 23 2009, IP COM JOURNAL N° 000182396D published on Apr. 29, 2009, IP COM JOURNAL N° 000189542D published on Nov. 12 2009, IP COM Journal N° IPCOM000011179D published on Mar. 4, 2004), and their mixtures. The above documents are incorporated by reference in their entirety.

By way of non-limiting example, at least one UV filter or UV filter system may include (listed by INCI name): dibenzoylmethane compounds such as butylmethoxydibenzoylmethane (for example, as sold under the trade name Parsol 1789® by DSM Nutritional Products, Inc.) and isopropyldibenzoylmethane; para-aminobenzoic compounds such as ethyl PABA, ethyl dihydroxypropyl PABA, ethylhexyl diméthyl PABA (sold under the name ESCALOL 507® by ISP), and glyceryl PABA; salicylic derivatives such as homosalate (sold under the commercial name Eusolex HMS by Rona/EM Industries) and ethylhexyl salicylate (sold under the commercial name NEO HELIOPAN OS by SYMRISE); cinnamic derivatives such as ethylhexyl methoxycinnamate (sold under the commercial name PARSOL MCX by DSM NUTRITIONAL PRODUCTS), isopropyl methoxy cinnamate, isoamyl methoxy cinnamate (sold under the commercial name NEO HELIOPAN E 1000 by SYMRISE), and cinoxate, diisopropyl methylcinnamate; derivatives of β,β-diphenylacrylate such as octocrylene (sold under the commercial name UVINUL N539 by BASF) and etocrylene (sold under the commercial name UVINUL N35 by BASF);

and hexyl 2-(4-diethylamino-2-hydroxybenzoyl) benzoate (sold under the commercial name UVINUL A Plus or in the form of a mixture with octylmethoxycinnamate under the commercial name UVINUL A+B by BASF); benzylidenecamphor derivatives such as 3-Benzylidene camphor (manufactured under the commercial name MEXORYL SD by CHIMEX), 4-Methylbenzylidene camphor (sold under the commercial name EUSOLEX 6300 by MERC), and polyacrylamidomethyl benzylidene camphor (manufactured under the commercial name MEXORYL SW by CHIMEX); phenyl benzotriazole derivatives such as drometrizole trisiloxane (sold under the commercial name Silatrizole by RHODIA CHIMIE); triazine derivatives such as bis-ethylhexyloxyphenol methoxyphenyl triazine (sold under the commercial name TINOSORB S by BASF), ethylhexyl triazone (sold under the commercial name UVINUL T150 by BASF), diethylhexyl butamido triazone (sold under the commercial name UVASORB HEB by SIGMA 3V), 2,4,6-tris(4'-amino benzalmalonate de dineopentyle)-s-triazine, 2,4,6-tris-(diisobutyle-4'-amino benzalmalonate)-s-triazine, and 2,4-bis (dineopentyle-4'-aminobenzalmalonate)-6-(4'-aminobenzoate de n-butyle)-s-triazine; triazine silicones substituted by two aminobenzoates groups such 2,4-bis-(n-butyl 4'-aminobenzalmalonate)-6-[(3-{1,3,3,3-tetramethyl-1-[(trimethylsilyloxy]disiloxanyl}propyl)amino]-s-triazine (and others as described in the patent EP0841341); anthranilic derivatives such as menthyl anthranilate (sold under the commercial name NEO HELIOPAN MA by SYMRISE), imidazoline derivatives such as ethylhexyl dimethoxybenzylidene dioxoimidazoline propionate; benzalmalonate derivatives such as di-neopentyl 4'-methoxybenzalmalonate and polyorganosiloxane with benzalmalonate functions such as Polysilicone-15 (sold under the commercial name PARSOL SLX by DSM NUTRITIONAL PRODUCTS); derivatives of 4,4-diarylbutadiene such as 1,1-dicarboxy (2,2'-diméthyl-propyl)-4,4-diphénylbutadiène; benzoxazole derivatives such as 2,4-bis-[5-1(diméthylpropyl)benzoxazol-2-yl-(4-phenyl)-imino]-6-(2-ethylhexyl)-imino-1,3,5-triazine (sold under the commercial name Uvasorb K2A by Sigma 3V); lipophilic merocyanine derivatives such as Octyl-5-N,N-diethylamino-2-phenysulfonyl-2,4-pentadienoate; terephthalylidene dicamphor sulfonic acid (Sold under the commercial name Mexoryl SX by CHIMEX; and drometrizole trisiloxane (Sold under the commercial name Mexoryl XL by RHODIA).

In one embodiment, the at least one UV-A filter is avobenzone and at least one UV-B filter includes, consists essentially of, or consists of octisalate, octocrylene, and/or homosalate. In another embodiment, the UV-A filter is avobenzone and the UV-B filter includes, consists essentially of or consists of at least two of octisalate, octocrylene, and homosalate. In still another embodiment, the UV filter system including the UV-A and the UV-B filters includes, consists essentially of, or consists of each of avobenzone, octisalate, octocrylene, and homosalate.

The composition may include any suitable amount of the at least one UV filter. In one embodiment, the composition includes at least about 1 wt %, at least about 3 wt %, at least about 5 wt %, at least about 7 wt %, at least about 10 wt %, less than about 35 wt %, less than about 30 wt %, less than about 25 wt %, less than about 20 wt %, less than about 15 wt %, and/or less than about 12 wt % of the at least one UV filter.

In some embodiments, the UV filter system is comprised of the following combination of UV filters: octocrylene, avobenzone, octisalate, and homosalate, and optionally oxybenzone; wherein the ratio of each filter relative to avobenzone is as follows:

the ratio of octocrylene to avobenzone is 1.6:1.0 to 2.4:1.0;

the ratio of oxybenzone to avobenzone 0.0:1.0 to 0.016:1.0;

the ratio of octisalate to avobenzone is 1.3:1.0 to 2.0:1.0; and the ratio of homosalate to avobenzone is 2.3:1.0 to 3.6:1.0.

In particular the ratio of the ratio of each filter relative to avobenzone is about: 2.0:1.0:0.0:1.7:3.0 (octocrylene:avobenzone:oxybenzone:octisalate:homosalate).

In one embodiment the UV filters are present in the following percentages by weight relative to the entire weight of the sunscreen composition:

at least 1 wt %, at least 2 wt %, at least 3 wt %, at least 4 wt %, at least 5 wt %, less than 12 wt %, less than 11 wt % less than 10 wt %, less than 9 wt %, less than 8 wt %, less than 7 wt %, and/or less than 6 wt % octocrylene;

at least 0.5 wt %, at least 1 wt %, at least 2 wt %, less than 5 wt %, less than 4 wt %, and/or less than 3 wt % avobenzone;

at least 0.5 wt %, at least 1 wt %, at least 2 wt %, at least 3 wt %, at least 4 wt %, less than 8 wt %, less than 7 wt %, and/or less than 5 wt % octisalate; and at least 1 wt %, at least 2 wt %, at least 3 wt %, at least 4 wt %, at least 5 wt %, less than 15 wt %, less than 12 wt % less than 10 wt %, less than 9 wt %, less than 8 wt %, and/or less than 7 wt % homosalate.

In another embodiment the UV filters are present in the following percentages by weight relative to the entire weight of the sunscreen composition: about 5.9 wt. % octocrylene; about 3.0 wt. % avobenzone; about 4.9 wt. % octisalate; and about 8.8 wt. % homosalate. Typically, the sunscreen compositions are essentially free of oxybenzone, or have less than 1.0, 0.5, 0.25, or 0.05 wt. % oxybenzone.

SPF Booster

The at least one SPF booster may include any suitable material, including, but not limited to a plurality of light refracting bodies. The plurality of light refracting bodies may have any composition and conformation. In one embodiment, the conformation of the light refracting bodies is a hollow sphere. In a further embodiment, the hollow sphere is filled with a substance having a refractive index which is different from the material from which the hollow sphere itself is made, yielding a structure which refracts UV radiation. In another embodiment, the composition of the light refracting bodies, specifically the material from which the hollow sphere itself is made, includes a styrene-acrylate copolymer composition. In a further embodiment, the composition of the light refracting bodies is a latex. In one embodiment, the at least one SPF booster may be present in the composition in the amount of at least 0.1 wt %, at least 0.3 wt %, at least 0.5 wt %, at least 0.7 wt %, less than 2 wt %, less than 1.5 wt %, less than 1.2 wt %, and/or less than 1 wt %.

According to one particular embodiment of the invention, the light refracting bodies are constituted of a copolymer of styrene and (meth)acrylic acid or one of its alkyl esters under the INCI name Styrene/Acrylates Copolymer, such as the product sold under the tradename SUNSPHERES® powder by the company Dow chemical, which is an aqueous dispersion containing about 86 wt % of Styrene/Acrylates Copolymer in a mixture of about 11 wt % of PEG-8 Laurate, about 2.5 wt % of water, and about 0.5 wt % of Sodium Dodecylbenzenesulfonate.

In one embodiment, the SPF boosters suitable for use with the invention have a particle size which ranges generally from about 100 to about 380 nm, alternatively from about 150 to about 375 nm, alternatively from about 190 to about 350 nm, alternatively from about 251 to about 325 nm, the particle size being a volume-average particle size measured by a photon correlation spectrometer such as a Brookhaven BI-90 photon correlation spectrophotometer.

The light refracting bodies may possess any suitable void fraction, including, but not limited to, a void fraction of 0.1% to 50%, alternatively 5% to 50%. In some instances, the void fractions may be determined by comparing the volume occupied by the light refracting bodies after having been compacted from a diluted dispersion in a centrifuge, relative to the volume of non-void particles of the same composition.

Light refracting bodies which are hollow latex particles, according to one embodiment of the invention, are obtained from particles comprising at least one polymer for the core and at least one polymer for the shell. The core polymer and the shell polymer may be obtained from a single polymerization step or from a sequence of polymerization steps. Such hollow latex particles may be provided as part of an aqueous dispersion that is stabilized with at least one emulsifier.

The hollow latex particles may be prepared by any suitable method, including, but not limited to the conventional techniques of emulsion polymerization. Such processes are described especially in U.S. Pat. Nos. 4,427,836, 4,469,825, 4,594,363, 4,677,003, 4,920,160, and 4,970,241 or by the conventional techniques of polymerization that are described in the following patents and patent applications: EP 267726, EP 331421, U.S. Pat. Nos. 4,970,229 and 5,157,084. The above patents are incorporated by reference in their entirety.

The monomers used for the shell of the latex particles may include one or more unsaturated nonionic ethylenic units. Optionally one or more monoethylenically unsaturated monomers containing at least one carboxylic acid group may be polymerized in the shell. In one embodiment, the monomers constituting the shell are selected such that they exhibit a glass transition temperature (Tg) which is sufficiently high to withstand the void of the hollow latex particle. The glass transition temperature may be greater than 50° C., alternatively greater than 60° C., alternatively greater than 70° C. The glass temperature (Tg) may be determined by differential scanning calorimetry.

The monomers used in the emulsion polymerization for the core polymer of the hollow latex particles of the invention may include one or more monoethylenically unsaturated monomers containing at least one carboxylic acid group. The core may include at least 5% by weight of monoethylenically unsaturated monomers containing at least one carboxylic acid group, relative to the total weight of the core monomers. The core polymer may, for example, be obtained by emulsion homopolymerization of the monoethylenically unsaturated monomer containing at least one acid group or by copolymerization of two or three monoethylenically unsaturated monomers containing at least one acid group. In one embodiment, the monoethylenically unsaturated monomer containing at least one acid group is copolymerized with one or more ethylenically unsaturated nonionic monomers.

The core polymer or the shell polymer may contain from 0.1% to 20% by weight, and, in some embodiments, from 0.1% to 3% by weight, of polyethylenically unsaturated monomers, such as ethylene glycol di(meth)acrylate, allyl (meth)acrylate, 1,3-butanediol di(meth)acrylate, diethylene glycol di(meth)acrylate, trimethylolpropane tri(meth)acrylate, or divinylbenzene, relative to the total weight of the core monomers. Alternatively, the core polymer or the shell polymer may optionally contain from 0.1% to 60% by weight of butadiene, relative to the total weight of the core monomers.

The monoethylenically unsaturated monomers containing at least one carboxylic acid group may include, by way of example, acrylic acid, methacrylic acid, acryloyloxypropionic acid, (meth)acryloyloxypropionic acid, itaconic acid, aconitic acid, maleic acid or maleic anhydride, fumaric acid, crotonic acid, monomethyl maleate, monomethyl fumarate, and monomethyl itaconate.

In one embodiment, the monomer is selected from acrylic acid and methacrylic acid. The monoethylenically unsaturated nonionic monomers may include, by way of example, styrene, vinyl toluene, vinyl acetate, vinyl chloride, vinylidene chloride, acrylonitrile, (meth)acrylamide, $C_1$-$C_{20}$ alkyl esters of (meth)acrylic acid, and ($C_3$-$C_{20}$) alkenyl esters of (meth)acrylic acid, such as methyl (meth)acrylate, ethyl (meth)acrylate, butyl (meth)acrylate, 2-ethylhexyl (meth)acrylate, benzyl (meth)acrylate, lauryl (meth)acrylate, oleyl (meth)acrylate, palmityl (meth)acrylate, and stearyl (meth)acrylate. As used herein, "(meth)acrylic" denotes the general expression encompassing both methacrylic or acrylic, and "(meth)acrylate" denotes the general expression encompassing both methacrylate or acrylate.

The void of the core of the latex particles may be produced by swelling the core with a swelling agent comprising one or more volatile compounds. The agent penetrates the shell in order to swell the core. The volatile components of the swelling agent may be subsequently removed by drying the latex particles, thus creating a void within the particles. The agent is, in some embodiments, an aqueous base. Mention may be made, for example, of ammonia, ammonium hydroxide, alkali metal hydroxides, such as sodium hydroxide, and volatile amines, such as trimethylamine or triethylamine.

The hollow latex particles may be introduced into the composition with the swelling agent. In such an embodiment, the volatile compounds are removed when the composition is dried. The hollow latex particles may also be added to the composition after the volatile compounds of the swelling agent have been removed.

In one embodiment, the hollow latex particles are those described in U.S. Pat. No. 5,663,213 and patent application EP 1092421, which are hereby incorporated by reference in their entirety.

In another embodiment, the hollow spheres of the light refracting bodies of the SPF booster include glass microspheres. Glass microspheres used in the compositions may be essentially homogeneous and essentially uniform in sphericity. The glass microspheres may have any suitable mean particle size, including, but not limited to, a mean particle size of between about 5 μm and 70 μm, alternatively from about 10 μm to 20 μm. Glass microspheres may include hollow microspheres of calcium aluminum borosilicate (commercially available from Presperse Inc. under the tradename LUXSIL®), sodium borosilicate particulates (commercially available from PQ Corporation under the tradename Q-CEL 570), and calcium/sodium borosilicate hollow microspheres (commercially available from 3M under the tradenames ES 22 and 1K), calcium/sodium borosilicate microspheres (commercially available from 3M's under the tradename Scotchlite™ $K_{20}$ product).

In yet another embodiment, the light refracting bodies of the SPF booster include porous silica in the form of microparticles, in particular, spherical microparticles. The spherical microparticles of porous silica may have any suitable mean particle size, including, but not limited to, a mean particle size ranging from 0.5 μm to 20 μm, alternatively from 3 μm to 15 μm. Further, the microparticles may have any suitable specific surface, including, but not limited to, a specific surface ranging from 50 $m^2$/g to 1,000 $m^2$/g, alternatively from 150 $m^2$/g to 800 $m^2$/g. Also, the microparticles may have any suitable specific pore volume, including, but not limited to, a specific pore volume ranging from 0.5 ml/g to 5 ml/g, alternatively from 1 ml/g to 2 ml/g. By way of example, the porous silica spherical microparticles may include commercial products such as Silica Beads SB 150 from Myoshi, Sunsphere H-51 from Asahi Glass, Sunsil 130 from Sunjin, Spherica P-1500 from Ikeda Corporation, and Sylosphere from Fuji Silysia.

In one embodiment, the SPF booster includes at least one material selected from the group consisting of (co)polymers of (meth)acrylic acid, (meth)acrylates, and/or styrene, glass, and silica. In another embodiment, the SPF booster includes at least two materials selected from the group consisting of (co)polymers of (meth)acrylic acid, (meth)acrylates, and/or styrene, glass, and silica. In yet another embodiment, the SPF booster includes a (co)polymers of (meth)acrylic acid, (meth)acrylates, and/or styrene, glass, and silica. The (co)polymers of (meth)acrylic acid, (meth)acrylates, and/or styrene, may be made of poly(meth)acrylates, such as PMMA, a copolymer of (meth)acrylic acid and (meth)acrylates, and a copolymer of (meth)acrylic acid, (meth)acrylates, and styrene.

Oils/Emollients

Examples of oils/emollients that may be included in the sunscreen compositions include: hydrocarbon-based oils of plant origin, such as liquid triglycerides of fatty acids containing from 4 to 10 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, coriander oil, castor oil, avocado oil, caprylic/capric acid triglycerides, for instance those sold by the company Stearineries Dubois or those sold under the names Miglyol® 810, 812 and 818 by the company Dynamit Nobel, jojoba oil, shea butter oil and caprylyl glycol; synthetic esters and ethers, especially of fatty acids, for instance Purcellin oil, 2-octyldodecyl stearate, 2-octyldodecyl erucate, isostearyl isostearate; hydroxylated esters, for instance isostearyl lactate, octyl hydroxystearate, octyldodecyl hydroxystearate, diisostearyl malate or triisocetyl citrate; fatty alcohol heptanoates, octanoates or decanoates; polyol esters, for instance propylene glycol dioctanoate, neopentyl glycol diheptanoate and diethylene glycol diisononanoate; and pentaerythritol esters, for instance pentaerythrityl tetraisostearate, or isopropyl lauroyl sarcosinate, sold especially under the trade name Eldew® SL 205 by the company Ajinomoto; linear or branched hydrocarbons, of mineral or synthetic origin, such as volatile or non-volatile liquid paraffins, and derivatives thereof, petroleum jelly, polydecenes, isohexadecane, isododecane, hydrogenated polyisobutene such as Parleam® oil, or the mixture of n-undecane ($C_{11}$) and of n-tridecane ($C_{13}$) sold under the reference Cetiol® UT by the company Cognis; fluoro oils that are partially hydrocarbon-based and/or silicone-based, for instance those described in document JP-A-2 295 912; silicone oils, for instance volatile or non-volatile polymethylsiloxanes (PDMS) with a linear or cyclic silicone chain, which are liquid or pasty at room temperature, in particular volatile silicone oils, especially cyclopolydimethylsiloxanes (cyclomethicones) such as cyclohexadimethylsiloxane and cyclopentadimethyl siloxane; polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethyl siloxydiphenyl siloxanes, diphenyl dimethicones, diphenylmethyldiphenyltrisiloxanes or 2-phenylethyl trimethylsiloxy silicates, and polymethylphenylsiloxanes; mixtures thereof.

Additional examples include benzoic acid esters of $C_9$-$C_{15}$ alcohols, isononyl iso-nonanoate, $C_{12}$-$C_{15}$ alkyl benzoate, or any combinations thereof.

Specific examples of oils/emollients include cocoglyceride, cyclomethicone, dimethicone, dicapryl maleate, caprylic/capric triglyceride, isopropyl myristate, octyl stearate, isostearyl linoleate, lanolin oil, coconut oil, cocoa butter, olive oil, avocado oil, aloe extracts, jojoba oil, castor oil, fatty acid, oleic acid, stearic acid, fatty alcohol, cetyl alcohol, hexadecyl alcohol, diisopropyl adipate, hydroxybenzoate esters, benzoic acid esters of $C_9$-$C_{15}$ alcohols, isononyl iso-nonanoate, alkanes, mineral oil, silicone, dimethyl polysiloxane, ether, polyoxypropylene butyl ether, polyoxypropylene cetyl ether, $C_{12}$-$C_{15}$ alkyl benzoate, aryl alkyl benzoate, Isopropyl Lauroyl sarcosinate, and any combinations thereof.

In some embodiments, the oils/emollients may be present in an amount of at least 0.1 wt %, at least 0.5 wt %, at least 1 wt %, at least 2 wt %, at least 3 wt %, at least 4 wt %, at least 5 wt %, less than 30 wt %, less than 25 wt %, less than 20 wt %, less than 15 wt %, less than 12 wt %, and/or less than 10 wt %, based on the total weight of the composition.

Solvents

Examples of hydrophilic organic solvents that may be included in the sunscreen compositions include:

monohydric $C_1$-$C_8$ alcohols such as ethanol, propanol, butanol, isopropanol, isobutanol;

polyethylene glycols from 6 to 80 ethylene oxides such as propylene glycol, isoprene glycol, butylene glycol, glycerol, sorbitol;

mono or di-alkyl isosorbides such as dimethyl isosorbide;

Examples of amphiphilic organic solvents that may be included in the sunscreen compositions include: polypropylene glycol (PPG) like propylene glycol alkyl ester or alkyl ether of PPG like PPG-23 oleyl ether and PPG-36 oleate.

Further Ingredients

The composition may further include other ingredients for forming the emulsion, as well as to modify the aesthetics (including scent, visual appearance and feel) and other properties of the composition. Such other ingredients may include, but are not limited to, water, EDTA, preservatives, emulsifiers, thickeners, humectants, emollients, aesthetic modifiers, film formers, anti-oxidants, TEA, denatured alcohols, perfumes, pigments, and whatever additions may be beneficial or particular to the desired form of the compositions or final product.

Optional Powders

The composition may optionally include powders. The optional powders provide formulas that are smoother and softer on the skin. Representative powders include, but are not limited to talc, mica, magnesium carbonate, calcium carbonate, magnesium silicate, aluminum magnesium silicate, silica, titanium dioxide, zinc oxide, red iron oxide, yellow iron oxide, black iron oxide, polyethylene powder, methacrylate powder, polystyrene powder, silk powder, crystalline cellulose, starch, titanated mica, iron oxide titanated mica, bismuth oxychloride, and the like. Additional powders include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesiumstearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide. A representative powder includes, for example, polymethylsilsesquioxane. Powders may be present in the compositions in amounts generally ranging from about 0.1% to about 5% by weight or about 0.1% to about 10% by weight, based on the total weight of the composition.

Composition

The composition may be any suitable composition, including, but not limited to, a skincare composition, a hair care composition, a sunscreen composition, a skin-tanning composition, a cosmetic composition, a make-up composition, a lip balm, a skin facial peeling composition, a moisturizing composition, an anti-aging skincare composition, or a combination thereof.

The above lists are only examples and are not limiting.

Examples

The method of making each of the examples provided in Table 1 is generally the same. In the examples of Table 1 the contents of phase A were combined in a mixer and heated to about 50 degrees Celsius with stirring and homogenization for about 15 minutes. In a side-kettle the contents of phase B were heated until a clear oil formed (65-75 degrees Celsius). Phase B is then combined with phase A with stirring and homogenization. After about 15 minutes heating was discontinued and stirring was continued while the composition was allowed to cool to room temperature.

All proportions of materials shown in the tables below are described in weight percent, unless otherwise indicated.

TABLE 1

| Phase | INCI US | Example 1 | Example 2 | Example 3 | Example 4 | Example 5 |
|---|---|---|---|---|---|---|
| A | AMMONIUM ACRYLOYLDIMETHYLTAURATE/VP COPOLYMER | 0.0475 | 0.0475 | 0.076 | 0.076 | 0.076 |
| A | BIS-PEG-18 METHYL ETHER DIMETHYL SILANE | 0.4995 | 0.4995 | 0.4995 | 0.4995 | 0.4995 |
| A | METHYL METHACRYLATE CROSSPOLYMER | 2 | 1 | 1 | 1 | 1 |
| A | CITRIC ACID | 0.05 | 0.05 | 0.05 | 0.05 | 0.05 |
| A | PEG-240/HDI COPOLYMER BIS-DECYLTETRADECETH-20 ETHER | 1.2 | 1.2 | 1.2 | 1.2 | 1.2 |
| | TOCOPHEROL | 0.0012 | 0.0012 | 0.0012 | 0.0012 | 0.0012 |
| A | SODIUM CITRATE | 0.15 | 0.15 | 0.15 | 0.15 | 0.15 |
| B | POLYGLYCERYL-6 DISTEARATE | 1.28 | 0.96 | 0.96 | | |
| B | POLYGLYCERYL-3 BEESWAX | 0.17 | 0.1275 | 0.1275 | | |
| A | POTASSIUM LAURATE | 0.0012 | 0.0012 | 0.0012 | 0.0012 | 0.0012 |
| A | CHLORPHENESIN | 0.2 | 0.2 | 0.2 | 0.2 | 0.2 |
| A | BUTYLENE GLYCOL | 5 | 5 | 5 | 5 | 5 |
| B | HOMOSALATE | 2 | 2 | 2 | 2 | 2 |
| A | PHENOXYETHANOL | 0.7 | 0.7 | 0.7 | 0.7 | 0.7 |
| A | BHT | 0.0005 | 0.0005 | 0.0005 | 0.0005 | 0.0005 |
| A | DISODIUM EDTA | 0.099 | 0.099 | 0.099 | 0.099 | 0.099 |
| B | GLYCERYL STEARATE | | 0.38 | 0.5 | 0.5 | 0.5 |
| B | CETYL ALCOHOL | 0.17 | 0.1275 | 0.1275 | | |
| B | OCTYLDODECANOL | 0.6 | 0.6 | 0.6 | 0.6 | 0.6 |
| B | CETEARYL GLUCOSIDE | | | | 1.5 | |
| A | GLYCERIN | 5 | 5 | 5 | 5 | 5 |
| B | OCTOCRYLENE | 4 | 4 | 4 | 4 | 4 |
| B | BUTYL METHOXYDIBENZOYLMETHANE | 2 | 2 | 2 | 2 | 2 |
| A | T-BUTYL ALCOHOL | 0.001 | 0.001 | 0.0016 | 0.0016 | 0.0016 |
| A | WATER | 74.4501 | 75.1901 | 74.921 | 74.921 | 74.921 |
| B | PEG-100 STEARATE | | 0.38 | 0.5 | 0.5 | 0.5 |
| B | POLYGLYCERYL-4 ISOSTEARATE | | | | | 1.5 |
| B | JOJOBA ESTERS | 0.38 | 0.285 | 0.285 | | |
| A | AMMONIUM ACRYLOYLDIMETHYLTAURATE/VP COPOLYMER | 0.0475 | 0.0475 | 0.076 | 0.076 | 0.076 |

In the comparative example of Table 2 the aqueous phase ingredients, ADEKA NOL GT-700, 1,3-butylene glycol and methylparaben, were combined and heated to about 80 degrees Celsius. The oil phase ingredients, UVA and UVB actives and ester oil, were combined separately and heated to about 80 degrees Celsius. The aqueous and oil phases were then combined in a mixer. The temperature was maintained at about 80 degrees Celsius and the composition was stirred for about 5 minutes. After about 5 minutes heating was discontinued and stirring was continued while the composition was allowed to cool to room temperature.

TABLE 2

| Phase | INCI US | Comparative Example 1 |
|---|---|---|
| A | PEG-240/HDI COPOLYMER BIS-DECYLTETRADECETH-20 ETHER | 1.0 |
| A | METHYLPARABEN | 0.2 |
| A | 1,3-BUTYLENE GLYCOL | 5.0 |
| A | WATER | 73.3 |
| B | BUTYL METHOXYDIBENZOYLMETHANE | 7.5 |
| B | ISOPROPYL LAURYL SARCOSINATE | 10 |
| B | PARA-AMINOBENZOIC ACID | 3 |

In the above examples the inventive compositions prepared at a temperature of about 50 degrees Celsius formed a substantially homogenous gel having a loss modulus is greater than the storage modulus (inverted). The inventive compositions were subjected to a 45 degree Celsius stability test for two weeks without undergoing phase separation.

The comparative compositions prepared at a temperature of about 80 degrees Celsius exhibited irreversible phase separation. In comparative example 1, no emulsion formed as the PEG-240/HDI Copolymer precipitated out at the higher temperature resulting in the formation of large oil phase agglomerates. The comparative composition was homogenized and subjected to a 45 degree Celsius stability test, resulting in phase separation within a day. Without being bound to a particular theory, it is believed the memory shape material, PEG-240/HDI copolymer bis-decyltetradeceth-20, underwent irreversible phase separation above a temperature of about 60 degrees Celsius.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A memory-shape skin-care composition comprising:
a) from 1 to 30 weight percent, based on the total weight of the composition, of a UV filter system, including a UV-A active material and a UV-B active material;
b) up to and including about 1.0 weight percent, based on the total weight of the composition, of a thickening emulsifier;
c) from 0.5 to 7 weight percent, based on the total weight of the composition, of a non-thickening emulsifier; and
d) from 0.5 to 7 weight percent, based on the total weight of the composition, of a memory-shape material that includes a polyethylene glycol/hexamethylene diisocyanate co-polymer;
wherein the composition includes an oil-in-water emulsion characterized as having a
loss modulus that is greater than a storage modulus.

2. The composition of claim 1, wherein the thickening emulsifier includes a non-branched polyol alkyl ester of glycerol or a non-branched sorbitan ester.

3. The composition of claim 1, wherein the non-thickening emulsifier includes a branched co-emulsifier including a branched polyol alkyl ester of glycerol and a branched sorbitan ester.

4. The composition of claim 3, wherein the non-thickening emulsifier includes a polyglyceryl stearate co-polymer.

5. The composition of claim 1, wherein the memory-shape material that includes a polyethylene glycol/hexamethylene diisocyanate co-polymer includes PEG-240/HDI copolymer bis-decyltetradeceth-20 ether present in the composition from 3 to 5 weight percent, based on the total weight of the composition.

6. The composition of claim 1, wherein the UV-A active material includes avobenzone and the UV-B active material includes octocrylene and homosalate.

7. The composition of claim 1, further comprising from 0.03 to less than 0.1 weight percent, based on the total weight of the composition, of at least one non-emulsifying thickener.

8. The composition of claim 7, wherein the at least one non-emulsifying thickener includes a cross-linked vinylpyrrolidone containing polymer.

9. A memory-shape skin-care composition comprising:
a) from 2 to 25 weight percent, based on the total weight of the composition, of a UV filter system that includes UV-A and UV-B active material, the UV filter system including avobenzone, octocrylene, and homosalate;
b) from 0.2 to 1.0 weight percent, based on the total weight of the composition, of a thickening emulsifier including a co-polymer including a glyceryl stearate/polyethylene glycol ester;
c) from 1 to 2 weight percent, based on the total weight of the composition, of a non-thickening emulsifier including a polyglyceryl stearate co-polymer; and
d) from 3 to 5 weight percent, based on the total weight of the composition, of a memory-shape material including a polyethylene glycol/hexamethylene diisocyanate co-polymer;
wherein the composition includes an oil-in-water emulsion characterized as having a
loss modulus that is greater than a storage modulus.

10. The composition of claim 9, further comprising from 0.03 to less than 0.1 weight percent, based on the total weight of the composition, of a non-emulsifying thickener that includes a cross-linked vinylpyrrolidone containing polymer.

11. The composition of claim 9, wherein the UV filter system further comprises at least one of octisalate, methylene bis-benzotriazolyl tetramethylphenol, diethylamino hydroxybenzoyl hexyl benzoate, ethylhexyl methoxycinnamate, isoamyl methoxycinnamate, ethyl hexyl salicilate, polysilicone-15, butyl methoxydibenzoylmethane, menthyl anthranilate, or ethylhexyl dimethyl PABA.

12. The composition of claim 9, wherein the polyglyceryl stearate co-polymer includes polyglyceryl-6 distearate.

13. The composition of claim 9, wherein the polyethylene glycol/ hexamethylene diisocyanate co-polymer includes PEG-240/HDI copolymer bis-decyltetradeceth-20 ether.

14. The composition of claim 10, wherein the cross-linked vinylpyrrolidone containing polymer includes ammonium acryloyldimethyltaurate/ vinylpyrrolidone co-polymer.

15. The composition of claim 2, wherein the non-branched polyol alkyl ester of glycerol or the sorbitan ester is selected from the group consisting of glycerol monostearate, glyceryl stearate/PEG ester, (2R,3R,4R,5S)-hexane-1,2,3,4,5,6-hexol;(Z)-octadec-9-enoic acid, sorbitan stearate/ sorbityl laurate, cetearyl glucoside, glyceryl stearate, steareth-100, glyceryl stearate citrate, and combinations thereof.

16. The composition of claim 2, wherein the non-branched polyol alkyl ester of glycerol or the sorbitan ester includes glyceryl stearate/PEG ester.

17. The composition of claim 3, wherein the branched co-emulsifier including the branched polyol alkyl ester of glycerol and the branched sorbitan ester includes polyglyceryl-4 isostearate, polyglyceryl-3 diisostearate, sorbitan isostearate, or sorbitan glyceryl isostearate.

18. The composition of claim 1, wherein the non-thickening emulsifier includes emulium meliferra, polyglyceryl-4 isostearate, polyglyceryl-4 diisostearate/polyhdroxyl stearate/sebacate, polyglyceryl-10 isostearate, polysorbate-20, polysorbate-40, or polysorbate-60.

19. The composition of claim 6:
wherein the ratio of octocrylene to avobenzone is 1.6:1.0 to 2.4:1.0; and
the ratio of homosalate to avobenzone is 2.3:1.0 to 3.6:1.0.

20. A memory-shape skin-care composition comprising:
a) from 2 to 25 weight percent, based on the total weight of the composition, of a UV filter system that includes UV-A and UV-B active material, the UV filter system including avobenzone, octocrylene, and homosalate;
b) from 0.2 to 1 weight percent, based on the total weight of the composition, of a thickening emulsifier including a glyceryl stearate/PEG ester;
c) from 1 to 2 weight percent, based on the total weight of the composition, of a non-thickening emulsifier including a polyglyceryl stearate co-polymer;
d) from 3 to 5 weight percent, based on the total weight of the composition, of a memory-shape material including a polyethylene glycol/hexamethylene diisocyanate co-polymer; and
e) from 0.03 to less than 0.1 weight percent, based on the total weight of the composition, of at least one non-emulsifying thickener including ammonium acryloyldimethyltaurate/vinylpyrrolidone co-polymer
wherein the composition includes an oil-in-water emulsion characterized as having a loss modulus that is greater than a storage modulus.

* * * * *